United States Patent [19]

Schmitt et al.

[11] 4,443,587
[45] Apr. 17, 1984

[54] 1,2,6-THIADIAZINE-3,5-DIONE-1,1-DIOXIDES AND THEIR USE AS POLYMERIZATION ACCELERATORS

[75] Inventors: Werner Schmitt; Robert Purrmann, both of Starnberg; Peter Jochum, Hechendorf; Heinz-Joachim Hübner, Wörthsee; Bernd Burger, Hechendorf, all of Fed. Rep. of Germany

[73] Assignee: Abitz, Morf, Gritschneder, Fed. Rep. of Germany

[21] Appl. No.: 349,769

[22] Filed: Feb. 18, 1982

[30] Foreign Application Priority Data

Feb. 27, 1981 [DE] Fed. Rep. of Germany ....... 3107577

[51] Int. Cl.³ .................... C08F 20/12; C08F 20/20
[52] U.S. Cl. .................... 526/146; 433/212; 526/205; 526/320; 526/323.1; 526/328; 526/329.7
[58] Field of Search .................. 526/146, 205

[56] References Cited

U.S. PATENT DOCUMENTS 2,956,997  10/1960  Teufel ................. 260/243
3,347,954  10/1967  Bredereck et al. ......... 525/21
4,302,381  11/1981  Omura et al. ............ 526/323.1

OTHER PUBLICATIONS

F. A. Cotton et al., Advanced Inorganic Chem., 4th Edt. p. 347, J. Wiley & Sons pub.
Chemical Abstracts, 90, 137873q (1979).

*Primary Examiner*—Harry Wong, Jr.

[57] ABSTRACT

1,2,6-Thiadiazine-3,5-dione-1,1-dioxides of the general formula

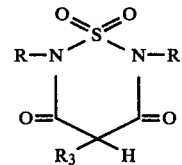

wherein each R and $R_3$ independently may be substituted or unsubstituted alkyl, alkenyl or substituted cycloalkyl are described. These compounds, as well as those wherein the R substituents additionally may be cycloalkyl or substituted or unsubstituted aryl, are useful as accelerators for the peroxidic polymerization of ethylenically unsaturated compounds, such as methacrylic acid compounds, and have particular utility in dental compositions.

7 Claims, No Drawings

1,2,6-THIADIAZINE-3,5-DIONE-1,1-DIOXIDES AND THEIR USE AS POLYMERIZATION ACCELERATORS

BACKGROUND OF THE INVENTION (a) Field of the Invention

This invention relates to novel 1,2,6-Thiadiazine-3,5-dione-1,1-dioxides (malonyl sulfamides) and to the use of 1,2,6-thiadiazine-3,5-dione-1,1-dioxides as accelerators for peroxides polymerization of ethylenically unsaturated compounds, such as methacrylic acid or acrylic acid compounds. The invention is of particular utility in formation of temporary dental crowns and bridges.

(b) State of the Art

U.S. Pat. No. 2,956,997 describes 1,2,6-thiadiazine-3,5-dione-1,1-dioxides (malonyl sulfamides) in which the substituent at one cyclic nitrogen is an aromatic or araliphatic hydrocarbon radical. The compounds described in that patent are characterized as having pharmaceutical properties, in particular antiphlogistic, antipyretic and analgesic activity, and therefore as being suited for treating rheumatic diseases.

German Auslegeschrift No. 1,495,520 described a process for polymerizing acrylic acid esters, methacrylic acid esters, acrylonitrile, vinyl acetate or styrene in the presence of organic peroxides in which barbituric acids, inter alia, may be used as accelerators. In addition a compound containing ionically bonded halogen and/or a copper compound may be used. The process described is used, for example, in the preparation of impression compositions, filling compositions, dentures, investments and fixatives in the fields of dentistry and dental technology.

SUMMARY OF THE INVENTION

This invention is directed to novel malonyl sulfamides having the following structure:

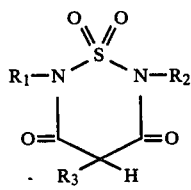

wherein $R_1, R_2$ and $R_3$, independently, are alkyl, alkenyl, substituted cycloalkyl or substituted alkyl, said alkyl substituents being limited to alkoxy, halogen, alkoxycarbonyl or cycloalkyl in the cases of $R_1$ and $R_2$. The invention is also directed to use of malonyl sulfamides, which have the formula:

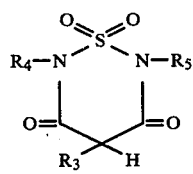

wherein $R_3$ is as above-defined and $R_4$ and $R_5$ are substituted or unsubstituted alkyl, cycloalkyl or aryl or unsubstituted alkenyl, as peroxidic polymerization accelerators for ethylenically unsaturated compounds, particularly methacrylic and acrylic acid compounds.

Compositions polymerized in accordance with the invention may be used in temporary dental appliances.

DETAILED DESCRIPTION OF THE INVENTION

This invention provides novel malonyl sulfamides, that is 1,2,6-thiadiazine-3,5-dione-1,1-dioxides. Moreover this invention provides methods for accelerating the polymerization of ethylenically unsaturated compounds effected by peroxo compounds by means of both the novel malonyl sulfamides and certain other prior art malonyl sulfamides. When the malonyl sulfamides are employed as polymerization accelerators less temperature elevation than is observed with barbituric acid accelerators of the prior art is observed. Such relatively reduced temperatures are particularly beneficial where dental devices, such as temporary bridges and crowns, are formed in the mouth.

The novel compounds of the invention are 1,2,6-thiadiazine-3,5-dione-1,1-dioxides of the formula I:

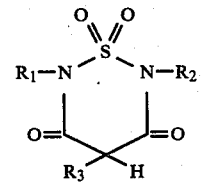

wherein $R_1$ and $R_2$ are independently selected from the group consisting of alkyl, alkyl substituted by alkoxy, halogen, alkoxycarbonyl or cycloalkyl, alkenyl and substituted cycloalkyl and $R_3$ is selected from the group consisting of alkyl, substituted alkyl, alkenyl and substituted cycloalkyl.

The 1,2,6-thiadiazine-3,5-dione-1,1-dioxides, which may be used to accelerate peroxidic polymerization of ethylenically unsaturated compounds, have the general formula II:

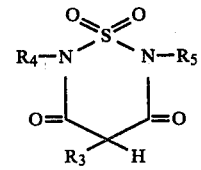

wherein $R_4$ and $R_5$ are independently selected from the group consisting of alkyl, substituted alkyl, alkenyl, cycloalkyl, substituted cycloalkyl, aryl and substituted aryl and $R_3$ is as defined above. The compounds of the general formula II are particularly useful as accelerators for the peroxidic polymerization of ethylenically unsaturated compounds, such as acrylic acid compounds and methacrylic acid compounds, most preferably polymerization of their esters.

If one of the radicals $R_1$ to $R_5$ in formulae I and II stands for unsubstituted alkyl, said radical may be straight or branched and may contain, for example, from 1 to 18 carbon atoms, preferably 1 to 10, and more preferably 1 to 6 carbon atoms. Alkyl radicals with 3 to 6 carbon atoms are especially preferred. Examples of suitable low molecular weight alkyl radicals are methyl, ethyl, propyl, i-propyl, n-butyl, t-butyl, s-butyl, i-butyl, n-pentyl and isoamyl.

If one of the radicals $R_1$ to $R_5$ is a substituted alkyl radical, the alkyl moiety of said radical preferably has the number of carbon atoms stated above for unsubstituted alkyl. When one of the radicals $R_1$ to $R_5$ is alkoxyalkyl or alkoxycarbonylalkyl, the alkoxy radical contains, for example, from 1 to 5 carbon atoms and preferably is methyl, ethyl, propyl, i-propyl, n-butyl, t-butyl, i-butyl, s-butyl, n-pentyl or isoamyl. When one of the radicals $R_1$ to $R_5$ is haloalkyl, halo means bromo, iodo, chloro or fluoro. When one of the radicals $R_3$ to $R_5$ stands for arylalkyl, the aryl preferably is phenyl or naphthyl. Especially preferred arylalkyl radicals are benzyl and phenylethyl. When one of the radicals $R_1$ to $R_5$ stands for cycloalkylalkyl, the cycloalkyl preferably contains four to seven carbons. Especially preferred cycloalkyls are cyclohexyl and cyclopentyl.

When one of the radicals $R_1$ to $R_5$ is alkenyl, $C_3$ to $C_5$ alkenyl radicals, especially allyl, are preferred. When one of the radicals $R_4$ or $R_5$ is an unsubstituted cycloalkyl, $C_4$ to $C_7$ cycloalkyl radicals, especially cyclopentyl and cyclohexyl, are preferred. When any one of $R_1$ to $R_5$ stands for substituted cycloalkyl, the above listed cycloalkyl radicals having one or more $C_1$ to $C_4$ alkyl, such as methyl, ethyl, propyl, n-butyl or i-butyl, fluoro, bromo, iodo, chloro or $C_1$ to $C_4$ alkoxy, especially methoxy, substituents are preferred.

In those cases where $R_4$ and/or $R_5$ are aryl, phenyl and naphthyl are preferred. The ring substituents preferably are $C_1$ to $C_4$ alkyl, especially methyl, halogen or $C_1$ to $C_4$ alkoxy, especially methoxy.

The radicals $R_1$ and $R_2$ and the radicals $R_4$ and $R_5$, respectively, are preferably identical. The following compounds are mentioned as individual examples of the malonyl sulfamides of the invention:
2,6-dimethyl-4-isobutyl-malonyl sulfamide (f.p. 59° C.)
2,6-dibutyl-4-isobutyl-malonyl sulfamide (f.p. −3° C.) ($n_D^{20}$ 1.4711)
2,6-diisobutyl-4-propyl-malonyl sulfamide ($n_D^{20}$ 1.4707)
2,6-dibutyl-4-propyl-malonyl sulfamide ($n_D^{20}$ 1.4728)
2,6-dimethyl-4-ethyl-malonyl sulfamide (f.p. 50° C.)
2,6-dioctyl-4-isobutyl-malonyl sulfamide ($n_D^{20}$ 1.4630)

The compounds of Formulae I and II can be prepared by one of the processes described in U.S. Pat. No. 2,956,997. For example, they may be prepared by reaction of the corresponding malonic acid compound or a derivative of such a compound with a corresponding substituted sulfamide.

When polymerization is effected, the malonyl sulfamides of formulae I and II are used in concentrations of from 0.1 to 15% by weight, preferably from 0.5 to 10% by weight, based on the polymerizable monomers. The malonyl sulfamides must be selected such that they are sufficiently soluble in the monomer to be hardened.

The peroxo catalysts employed for polymerization are mostly organic peroxides, such as benzoyl peroxide or lauroyl peroxide. To enhance acceleration, the polymerization is preferably carried out in the presence of heavy metal compounds and ionic halogen or pseudohalogen. Copper is an especially suitable heavy metal; the chloride ion an especially suitable halide. The amounts of peroxo catalysts, optionally together with desensitizer, are 0.1 to 10, preferably 0.5 to 5% by weight; of heavy metal (suitably in the form of soluble organic compounds) 1 to 200 ppm., preferably 10 to 100 ppm., and of (pseudo) halide ions (suitably in the form of a soluble salt) 0.01 to 1% by weight, preferably 0.05 to 0.5% by weight, each based on the polymerizable proportion of the composition. In conventional manner the polymerizable compositions may additionally contain fillers dyestuffs, pigments, opacifiers and/or light and heat stabilizers.

In order to reduce polymerization shrinkage, to increase the mechanical strength and to adapt the color to that of natural teeth fillers, dyestuffs and/or fluorescent substances are added to the monomer prior to polymerization thereof. Suitable fillers are, inter alia, polymethyl methacrylate beads pigmented ready for use or other pulverized organic polymers, as well as inorganic fillers, especially ultrafine filler such as pyrogenic silica.

The polymers obtained with the use of the compounds of the invention exhibit high color stability and good mechanical strength. Furthermore, during cold polymerization of monomers such as methacrylic acid esters, the compounds of formulae I and II improve upon barbituric acid compounds in that the temperature rises to a lesser degree during the polymerization process. This is particularly advantageous in dentistry when larger amounts of composition must be polymerized in the mouth, e.g. when making temporary crowns and bridges. In dental technology, mono-, di- or polyfunctional methacrylic acid esters are commonly employed as polymerizable monomers, e.g. the dimethacrylate esters of German Pat. No. 1,921,969 or of German Offenlegungsschrift No. 2,414,258. Overall, as shown below by comparative tests, use of the accelerators of the invention, produces semipermanent dental crowns and bridges which possess mechanical properties superior to the prior art materials with comparatively low rise of temperature during the polymerization.

The following examples are illustrative of the invention:

EXAMPLE 1

Accelerator Preparation 208 g N,N′-Di-n-butyl sulfamide are dissolved in 400 ml. toluene. 144 g freshly distilled malonyl dichloride are added dropwise at room temperature with stirring. Gas evolves accompanied by a slight increase in temperature. After the end of the dropwise addition, the mixture is heated to 70° C. For 7 hours. The solvent is removed in a vacuum. The residue is dissolved in 2N sodium hydroxide solution and extracted with toluene. The aqueous phase is acidified with hydrochloric acid, extracted with dichloromethane, dried over sodium sulfate, and freed from solvent. The crude product is distilled under vacuum; at 0.4 mbar 175 g 2,6-di-n-butyl-malonyl sulfamide (I) pass over between 110° and 115° C. The acid equivalent upon titration with sodium methylate is 275 (theoretical=276).

30.5 g of the distillation product (I) are dissolved in 100 ml. glacial acetic acid, mixed with 15.8 g isobutyraldehyde, and maintained at 80° C. for 5 hours. Then the reaction mixture is poured into 1 liter water, the mixture is extracted with dichloromethane, dried over sodium sulfate, and the solvent is removed. It is dissolved once more in 1 liter water and extracted, dried and freed from solvent as before. One obtains 29 g 2,6-di-n-butyl-4-isobutylidene-malonyl sulfamide (II); the acid equivalent is 333 (theoretical=330); $n_D^{20}$=1.4887.

10 g of the alkylidene compound (II) are dissolved in 20 ml. tetrahydrofurane and together with about 2 ml. Raney nickel the solution is introduced into a metallic autoclave under nitrogen. After introduction of 50 bar of hydrogen, the autoclave is shaken at 100° C. for 1 minute; the pressure drop is about 10 bar. After cooling the reaction product is decanted, the solvent removed, and the residue taken up in 2N sodium hydroxide solution. After shaking with toluene the product is acidified with 2N hydrochloric acid, extracted with dichloromethane, dried over sodium sulfate, and freed from solvent. The crude product is purified by vacuum distillation (0.3 mbar, 130° C.). One obtains 3.5 g 2,6-di-n-butyl-4-isobutyl-malonyl sulfamide; the acid equivalent is 331 (theory=330); $n_D^{20}$=1.4711; f.p.=$-3°$ C.

$^1$H-NMR (60 Mega-c.p.s., int. TMS)
0.8–1.13$\delta$, multiplett (m), 12 H
1.13–2.07$\delta$, m, 11 H
3.63–4.15$\delta$, m, 5 H The following compounds may be prepared analogously;
2,6-dimethyl-4-ethyl-malonyl sulfamide (f.p. 50° C.)
2,6-dimethyl-4-isobutyl-malonyl sulfamide (f.p. 59° C.)
2,6-diethyl-4-butyl-malonyl sulfamide ($n_D^{20}$=1.4761)
2,6-dipropyl-4-ethyl-malonyl sulfamide ($n_D^{20}$=1.4760)
2,6-dipropyl-4-propyl-malonyl sulfamide ($n_D^{20}$=1.4741)
2,6-dibutyl-4-ethyl-malonyl sulfamide ($n_D^{20}$=1.4733)
2,6-dibutyl-4-butyl-malonyl sulfamide ($n_D^{20}$=1.4729)
2,6-diisobutyl-4-ethyl-malonyl sulfamide ($n_D^{20}$=1.4719)
2,6-diisobutyl-4butyl-malonyl sulfamide (f.p. 31° C.)
2,6-diisobutyl-4-benzyl-malonyl sulfamide (f.P. 73° C.)
2,6-bis-($\gamma$-methoxy-propyl)-4-isobutyl-malonyl sulfamide ($n_D^{20}$=1.4739)
2,6-dioctyl-4-isobutyl-malonyl sulfamide ($n_D^{20}$=1.4630)
2,6-dilauryl-4-isobutyl-malonyl sulfamide ($n_D^{20}$=1.4674)
2,6-dibutyl-4-lauryl-malonyl sulfamide ($n_D^{20}$=1.4622)

EXAMPLE 2

A casting resin may be made as follows: A solution is prepared from 400.0 g 2,2-bis[p-($\gamma$-hydroxy-propoxy) phenyl] propane dimethacrylate, 4.8 g ($\beta$-phenyl-ethyl)-dibutyl-ammonium chloride and 80.0 mg bis(1-phenyl-pentane-1,3-dionato) copper (II). For stabilization against premature polymerization and for standardization of reactivity 50 ppm. p-methoxyphenol are added to the mixture; when stored in a closed container it is stable for several months.

2 g of the above solution are quickly mixed homogeneously with 80 mg of 50% benzoyl peroxide paste (in phthalate) and 80 mg 2,6-dimethyl-4-isobutyl-malonyl sulfamide (mixed 1:1 with phthalate). The resulting composition is flowable for about 2 minutes and is poured into a cylindrical metallic mold. After about 8 minutes a hard, clear molding is obtained with little heat development.

EXAMPLE 3

2.0 g of the solution prepared in Example 2 are homogeneously blended with 80.0 mg 20% lauroyl peroxide paste (in phthalate) and 80.0 mg 2,6-dibutyl-4-isobutyl-malonyl sulfamide (prepared according to Example 1). The composition remains flowable for about 2 minutes. The resulting mixture sets with little heat development and is suitable for the production of hard, clear, shaped articles of stable color.

EXAMPLE 4

The solution prepared in Example 2 is kneaded with 85 g silanized ultrafine silica (dyed to the color of teeth) to form a still-flowable paste. 680 mg of said paste are homogeneously blended with 20 mg 20% lauroyl peroxide paste (in phthalate) and 20 mg 2,6-dibutyl-4-isobutyl-malonyl sulfamide. The mixture is processable for about 2.5 minutes and is suitable for producing parts of dentures.

EXAMPLE 5

1.36 g of the activated mixture prepared according to Example 4 are introduced by means of a syringe into an alginate or silicone impression, which was made before the preparation of the bridge abutment teeth and in which a deep groove is incised between the impressions of the bridge abutment teeth. The filled impression is inserted into the patient's mouth and, after setting has started (i.e., about 3 to 4 minutes after blending was started), is removed together with the molding from the patient's mouth. During setting there is only slight temperature rise.

About 6 minutes after the start of blending, the semi-permanent bridge can be finished in the usual way. The product is a cosmetically satisfactory and mechanically stable denture part of high color stability which can be repaired, if need be.

EXAMPLE 6

The hardened material for semi-permanent crowns and bridges obtained according to Example 4 (hereafter designated "(A)") was compared with commercially available materials. Material (B) is epimin-based ("SCUTAN", manufactured by ESPE); material (C) is acrylate-based ("TRIM", manufactured by Bosworth).

| Material | Resistance to Pressure | Resistance to Flexing | Surface Hardness |
| --- | --- | --- | --- |
| (A) (invention) | 240 MPa | 100 MPa | 120 MPa |
| (B) epimine-based (prior art) | 75 MPa | 70 MPa | 85 MPa |
| (C) acrylate-based (prior art) | 70 MPa | 60 MPa | 40 MPa |

EXAMPLE 7

The advantages of the malonyl sulfamides of the invention in cold setting are demonstrated by the below tests:

80 mg of bis(1-phenyl-pentane-1,3-dionato)copper (II) and 4.8 g $\beta$-phenylethyl-dibutyl-ammonium chloride are dissolved in 400 g 2,2-bis[p-($\gamma$-hydroxy-propoxy)phenyl] propane dimethacrylate. Said solution is kneaded with 85 g silanized ultrafine silica. To 1.36 g of said paste there is added 40 mg of 50% benzoyl peroxide (in phthalate) and the barbituric acid or the malonyl sulfamide listed in the Table. The amount of accelerator is determined in a preliminary test so that setting (gelling) begins after about 2.5 minutes. A 1 ml. plastic mold which is covered with a funnel as draft protection is filled with the activated mixture. A fine thermocouple is inserted into the funnel opening and the course of temperature during setting is read from a suitable measuring instrument. The maximum temperature is listed in the following Table.

| Accelerator | Begin of Setting (min./sec.) | End of Setting (min./sec.) | Peak Temperature °C. |
| --- | --- | --- | --- |
| 1,5-dimethyl-3-iso-butyl barbituric | 2'30" | 8' | 53 |

| Accelerator | Begin of Setting (min./sec.) | End of Setting (min./sec.) | Peak Temperature °C. |
|---|---|---|---|
| acid | | | |
| 2,6-dimethyl-4-iso-butyl-malonyl sulfamide | 2'30" | 5' | 45 |
| 2,6-dibutyl-4-iso-butyl-malonyl sulfamide | 2'30" | 6' | 45 |

Starting out from room temperature, the temperature rise in case of barbituric acid is more than one third higher than malonyl sulfamides of the invention. This lower temperature rise is of special significance in dentistry because the development of heat during polymerization in the mouth may harm the tooth stumps which have already been subjected to great stress during grinding.

We claim:

1. In a method for the peroxidic polymerization of ethylenically unsaturated compounds selected from the group consisting of acrylic and methacrylic acid compounds useful in the formation of dental type molded articles including the steps of mixing such ethylenically unsaturated compounds with a peroxidic initiator and accelerator and polymerizing the resulting mixture in a mold, the improvement comprising use of a compound of the formula

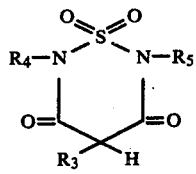

wherein
$R_4$ and $R_5$ independently are alkyl, substituted alkyl, alkenyl, cycloalkyl, substituted cycloalkyl, aryl, or substituted aryl, and
$R_3$ is alkyl, substituted alkyl, alkenyl, or substituted cycloalkyl, as an accelerator.

2. The method of claim 1 wherein the accelerator compound is present in an amount from 0.1 to 15% by weight based upon the ethylenically unsaturated compound being polymerized.

3. The method of claim 1 wherein the peroxo catalyst is selected from the group consisting of benzoyl peroxide and lauroyl peroxide.

4. The method of claim 1 wherein the polymerization is effected in the presence of 1 to 200 ppm heavy metal compound and 0.01 to 1% by weight ionic halogen or pseudohalogen as additional accelerators.

5. The method of claim 4 wherein the heavy metal is copper and the ionic halogen is chloride.

6. The method of claim 1 wherein the methacrylic acid compound is an ester.

7. The method of claim 1 wherein the ethylenically unsaturated compounds and the accelerator are mixed and are polymerized in a mold to form a dental device.

* * * * *

UNITED STATES PATENT AND TRADEMARK OFFICE
CERTIFICATE OF CORRECTION

PATENT NO. : 4,443,587

DATED : April 17, 1984

INVENTOR(S) : Werner Schmitt; Robert Purrmann; Peter Jochum; Heinz-Joachim Hubner and Bernd Burger It is certified that error appears in the above-identified patent and that said Letters Patent are hereby corrected as shown below:

On the title item /73/ should read:

-- [73] Assignee: Espe Fabrik pharmazeutischer Praparate Gesellschaft mit beschrankter Haftung, Seafeld, Germany --.

Signed and Sealed this

Eleventh Day of December 1984

[SEAL]

Attest:

GERALD J. MOSSINGHOFF

Attesting Officer        Commissioner of Patents and Trademarks